United States Patent [19]
Kaufman

[11] Patent Number: 5,234,428
[45] Date of Patent: Aug. 10, 1993

[54] DISPOSABLE ELECTROCAUTERY/CUTTING INSTRUMENT WITH INTEGRAL CONTINUOUS SMOKE EVACUATION

[76] Inventor: David I. Kaufman, 743 College Ct., Los Altos, Calif. 94022

[21] Appl. No.: 713,070

[22] Filed: Jun. 11, 1991

[51] Int. Cl.⁵ ............................................. A61B 17/39
[52] U.S. Cl. ...................................... 606/45; 606/49; 604/35
[58] Field of Search ....................... 606/41, 42, 45, 49; 604/35

[56] References Cited

U.S. PATENT DOCUMENTS

| | | |
|---|---|---|
| 2,275,167 | 4/1939 | Bierman . |
| 2,808,833 | 10/1957 | August . |
| 2,888,928 | 6/1959 | Seiger . |
| 3,825,004 | 7/1974 | Durden, III . |
| 3,828,780 | 8/1974 | Morrison, Jr. . |
| 3,902,494 | 9/1975 | Haberlen et al. . |
| 3,906,955 | 9/1975 | Roberts . |
| 3,974,833 | 8/1976 | Durden, III . |
| 4,307,720 | 12/1981 | Weber, Jr. . |
| 4,347,842 | 9/1982 | Beale . |
| 4,545,375 | 10/1985 | Cline . |
| 4,562,838 | 1/1986 | Walker . |
| 4,683,884 | 8/1987 | Hatfield et al. . |
| 4,719,914 | 1/1988 | Johnson . |
| 4,850,352 | 7/1989 | Johnson . |
| 4,865,049 | 9/1989 | Gatti . |
| 4,911,159 | 3/1990 | Johnson et al. ............... 606/49 X |
| 5,085,657 | 2/1992 | Ben-Simhon ................. 604/35 X |

OTHER PUBLICATIONS

Olsen Electrosurgical Instruments and Accessories, Hospital Price List, 1991.

*Primary Examiner*—Lee S. Cohen
*Attorney, Agent, or Firm*—Howard L. Rose

[57] ABSTRACT

An electrosurgical pencil comprises a body having air flow passages through the body connectable at one end to a vacuum source and opening at their other ends into a shroud providing an annular opening about the electrode blade of the pencil, the shroud, blade and various passages being configured such that the air flow intake velocity into the shroud is at least approximately twice the diffusion velocity of smoke generated at an incision produced by the blade of the pencil.

19 Claims, 5 Drawing Sheets

DISPOSABLE ELECTROCAUTERY/CUTTING INSTRUMENT WITH INTEGRAL CONTINUOUS SMOKE EVACUATION

FIELD OF INVENTION

The present invention relates to surgical instruments providing evacuation of hazardous smoke generated by electrosurgical pencils, and more particularly to an instrument which maintains the versatility of the hand or foot-controlled electrosurgical pencil while providing continuous and simultaneous evacuation of smoke generated by the instrument.

BACKGROUND OF THE INVENTION

Nearly every surgical procedure employs electrosurgical techniques to diminish both blood loss and operating time. Small blood vessels are sealed by heat, obviating the need to meticulously and laboriously tie off by hand each blood vessel.

In using an electrosurgical pencil, either for coagulation of blood or for cutting through tissue, a large volume of smoke is generated. This smoke contains aerosolized and vaporized organic material, carbon particles, steam, and viable viral particles. This smoke raises concerns about exposure and transmission through the respiratory tract by inhalation of viable human papillomavirus, HIV (AIDS), Hepatitis B, and non-A, non-B hepatitis viral particles in the electrocautery smoke plume. Operating room face masks and face shields are, at best, only marginally protective. There is also concern that the vaporized organic material and carbon particles may be carcinogenic. Finally, the odor of burning flesh is offensive to those exposed to it. These problems have led to a long-felt universal desire for a solution to this occupational environmental health hazard that does not interfere with the necessary and established functions of each member of the operating team, that is inexpensive, effective, easy to set up and use, has no additional moving parts to slide or manipulate, and is disposable.

The usual operating team consists of a scrub nurse or technician, who passes instruments and sutures, and occasionally holds retractors and suctions blood; a surgeon, who performs the surgical procedure; and often, a surgical assistant or assistant surgeon, who holds retractors, cuts sutures, suctions blood, and otherwise assists the surgeon by providing an extra pair of hands. In addition, there is usually an anesthesiologist or anesthetist close to the operating field. When large volumes of smoke are generated by the electrosurgical pencil, either the scrub nurse or the surgical assistant will make an attempt to suction the smoke with a Yankaur or other suction instrument if their hands are free. The surgeon generally has the electrosurgical pencil in one hand, and a retractor or sponge in the other. All of the suction instruments in common usage have small apertures designed for liquids, and are relatively ineffective for suctioning smoke. In addition, because placing these suction instruments near the point of smoke generation blocks the surgeon's field of view, the smoke has usually had a chance to disperse widely, so that little of it reaches the aperture of the suction instrument. And finally, personnel usually do not have their hands free to attempt continuous suction of the smoke. This results in a heavy exposure to smoke of the entire surgical team.

Heretofore, attempts to solve the problem of effective smoke elimination have been expensive and/or cumbersome, and most often, mentioned as an afterthought to the function of suctioning blood and other liquids. The infectious and carcinogenic potential of smoke generated from an electrocautery instrument was not always appreciated, and prior art usually mentioned clearing smoke only to give the surgeon a clear field of vision, which, in fact, is rarely a problem. None of the prior art has been directed at eliminating the hazard of smoke inhalation by utilizing a design which, while adding no moving parts to a hand-switchable instrument, effectively, simultaneously, and continuously traps smoke in a 360° arc around the point where it is generated at the electrode blade tip before the smoke diffuses while leaving the surgeon's view unobstructed.

None of the prior art comprises a transparent addition to the functionality of the electrosurgical pencil while maintaining its hand-controlled cutting and cautery functions and its interchangeable bits. None of the prior art has the qualities of being inexpensive and disposable, and of requiring no extra training, setup time or packaging. Also, most prior art devices utilize a single hollow tube for both cautery and suction, which significantly diminishes the prior art's utility as an electrosurgical instrument, making the prior art unsuitable for cutting and unable to accept interchangeable bits, and, most importantly, unable to trap smoke effectively because the smoke disperses laterally away from the tube walls as it is generated.

U.S. Pat. No. 2,888,928 is a design for an instrument with a hollow shaft for suction and cautery. The shaft renders it unsuitable for cutting. It cannot accept interchangeable standard bits, is expensive to manufacture and clean, and it is not meant to be disposable. In addition, its hollow shaft design renders it marginally effective for trapping smoke.

U.S. Pat. No. 4,307,720 is an electrocautery instrument with a suction tube associated with and located in close proximity to a retractable cauterizing blade. While this device may have some usefulness, it is relatively expensive and awkward to use. The suction port consists of a single small aperture located below the electrode blade, making it unable to trap smoke in anything close to the 360° arc around the electrode blade that is necessary for it to be effective.

U.S. Pat. No. 3,906,955 is an electrocautery instrument with a manually retractable suction tube located beneath and in close proximity to a cauterizing blade. Its moving parts make it expensive to manufacture and cumbersome to operate. In addition, the position of the suction port below the electrode blade make it poorly suited for suctioning smoke. The retractable suction tube is meant to extend out to the cauterized area for suctioning blood and tissue debris before or after cauterization, but not during.

U.S. Pat. Nos. 2,808,833, 3,825,004, 3,828,780, 3,902,494, 3,974,833 and 4,347,842 are combined electrocoagulator-suction instruments utilizing a hollow shaft for suctioning blood and other liquids from the operating field and for cauterizing. They have no utility for evacuating smoke from the operating field, nor are they useful for cutting through tissue.

U.S. Pat. No. 4,865,049 is a smoke-eliminating shield with no electrosurgical function. It does not prevent smoke from dispersing in all directions before attempting to trap it. It also requires additional packaging and setup time, which at an average of $15 per minute for operating room time, becomes expensive for the patient.

U.S. Pat. No. 4,683,884 is conceived as a noise attenuating smokeless surgical device. It specifies an electric cable running through the wall of the tubular housing, rather than in an axial line through the center of the device, thereby offsetting the blade where it would be both difficult to see and awkward to use. There is no allowance for electrical hand switches, nor is the means of attaching the blade to the electric cable in the suction housing specified. The position of the blade relative to the suction intake would cause the tubular housing to obscure the blade tip from the surgeon's vision. Although the design may function as a noise-suppression device, it has questionable utility as an electrosurgical instrument, and none as a hand switchable instrument. In addition, Hatfield's invention is designed for noise suppression, which is not in the area of the present invention.

U.S. Pat. No. 4,719,914 is essentially a hollow tube with an opening at one end to which a vacuum may be applied, and with a tapered nose portion at the other end through which an electrocauterizing blade protrudes. This nose portion has a plurality of openings for withdrawing smoke. Application of the vacuum through the nose portion openings is achieved by moving a sliding sleeve along the body of the instrument so that it extends over the openings in the nose portion and surrounds the cauterizing blade. Because this design is comprised of a tube sliding over a tube, the outer tube, which forms the extensible hood, must have walls that are either parallel to each other, or flare out. If the walls of the hood tapered inward, than it would not be able to retract back onto the body of the instrument. In designing and testing the present invention, early prototypes employed a design which duplicated Johnson's hood in the extended position with parallel sides. Tests of this configuration conclusively demonstrated that for the instrument to effectively aspirate smoke generated at the electrocautery blade tip, the aperture of the hood had to be so close to the tip of the blade that, when held in a position that would actually be used on the surgical field, the extensible sleeve obscured the tip of the blade, which is unacceptable.

U.S. Pat. No. 4,850,352 is a continuation-in-part of U.S. Pat. No. 4,719,914 cited above. It applies the same design of an extensible sleeve to a laser surgical instrument. The objections cited for the co-patent above apply equally. In addition, a laser is aimed indirectly through an optical system such as an operating microscope. An electrosurgical blade is guided under the direct vision of the surgeon. A laser also does not have electrical switches that can come in contact with conductive liquids. The two instruments, therefore, cannot be construed as being interchangeable because they have substantially different requirements for intrinsic electrical safety and for the safe placement of a beam versus a blade.

OBJECTS AND ADVANTAGES

Accordingly, several objects and advantages of my invention are as follows:

A principle object and advantage of this invention is to provide a single surgical instrument with two complimentary functions that do not interfere with each other.

Another object of the invention is to provide an instrument that is capable of simultaneously, continuously, and effectively evacuating from the surgical field hazardous smoke generated by the instrument in its use as an intrinsically safe hand or foot actuated electrosurgical pencil with interchangeable electrode blades.

Still another object of the present invention is to provide an instrument whose use produces smoke which is evacuated by the instrument in a 360° arc around the point of smoke generation at its electrode blade tip without obscuring the blade tip from the surgeon's view.

It is yet another object of the present invention to provide a surgical instrument for cutting and cauterizing having no additional moving parts to slide or to manipulate, which completely maintains the ergonomic design, utility and convenience of a hand switchable electrosurgical pencil alone and which isolates sealed electrical switches and cables from the suction channels.

Another object and advantage of the invention is to provide an instrument which is economically produced, is ready to use by merely attaching it to a standard electrical generator providing a high frequency signal and to a standard vacuum source, and is disposable after use, insuring a new sterile instrument for each operation.

An even further object and advantage is to provide an instrument which has been designed using aerodynamic principles to maximize airflow through the instrument by optimizing the shape, position, and cross-sectional diameter of the entry aperture and internal channels and to minimize airflow turbulence by appropriate shaping of the entry aperture and internal channels, all while maintaining the shape and functionality of an electrosurgical pencil.

A still further object of the invention is to provide a shroud for the electrode blade of a surgical instrument providing an aerodynamically optimized radius of the leading edge of the entry aperture which gives the instrument a smooth, rounded surface which will not catch or traumatize tissue or blood vessels that it comes in contact with.

Another object and advantage is to provide an easily attached suction intake cone extension that uses a snap-on fastener so that effective and unobtrusive smoke evacuation is maintained when six-inch extended blade or needle electrodes are needed for electrosurgery in a deep body cavity.

It is yet another object of the present invention to utilize the concepts of the present invention to reduce inhalation of smoke generated as a result of use of an electrically heated electrode in a hand held instrument regardless of the use to which such instrument is put.

Still another object of the present invention is to provide a shroud for the electrode blade of a surgical instrument to provide acquisition of smoke generated by use of the blade, said shroud being immovable but permitting easy access to the end of the blade for cleaning purposes.

BRIEF DESCRIPTION OF THE INVENTION

The instrument of the present invention uses standard 2.4 mm interchangeable electrosurgical electrodes, is compatible with all standard radio frequency power supplies, incorporates a standard vacuum tubing connector for use with standard 5 mm internal diameter non-conductive tubes for connection via standard fittings to the standard vacuum canisters found in all operating rooms, which effectively evacuates smoke using standard vacuum pressures and flows specified for all operating rooms.

Specifically the instrument is a throw-away device and comprises a perfectly clear plastic sleeve or shroud permanently secured to and extending from the end of a heated electrosurgical pencil, the pencil having passages for connection to a vacuum source. The instrument is designed to have inlet velocities at the entrance to the sleeve two to three times the velocity of spread of the smoke while maintaining maximum possible inlet area. The expansion velocity of the smoke is approximately 10 to 15 feet per second. The visual clearance angle is maintained at approximately 25°; the critical design ratio being inlet diameter to length of blade protruding beyond the sleeve. The sleeve is tapered inwardly toward the tip of the blade to maintain specific area ratios whereby the desired velocities at the entrance to the sleeve and at the entrance to the vacuum passages on the pencil are achieved. Further the device is configured such that total pressure loss throughout the vacuum system is less than the available suction pressure.

BRIEF DESCRIPTION OF THE DRAWINGS

These features and objects of the invention, as well as others, will become apparent to those skilled in the art by referring to the accompanying drawings.

DETAILED DESCRIPTION OF THE INVENTION

Figures 1, 2:
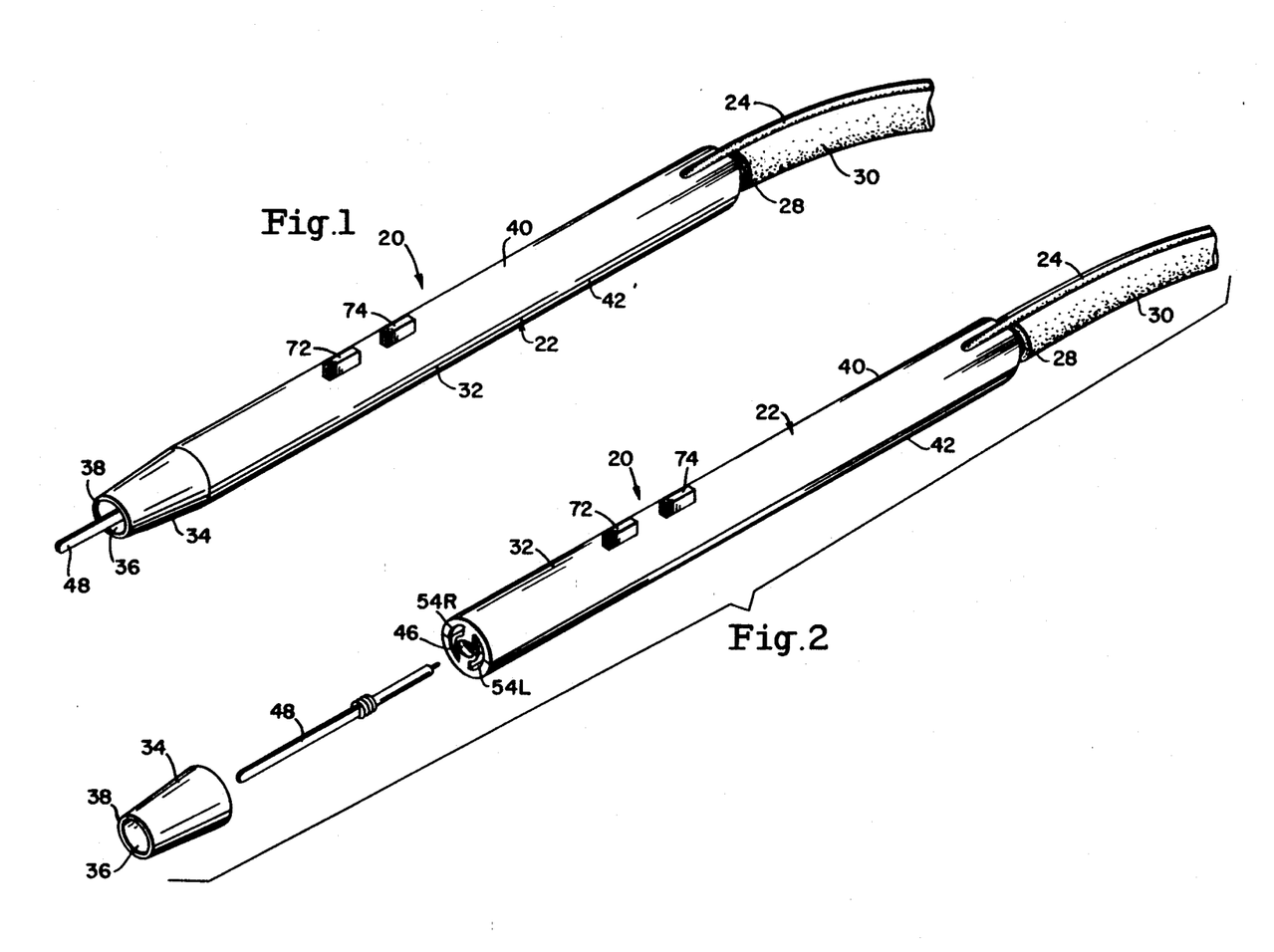
FIG. 1 is a perspective view of the electrosurgical pencil with integral smoke evacuation.
FIG. 2 is a perspective view of the electrosurgical pencil with the truncated suction intake cone exploded to reveal the external intake openings for the internal suction channels.
Figure 12:
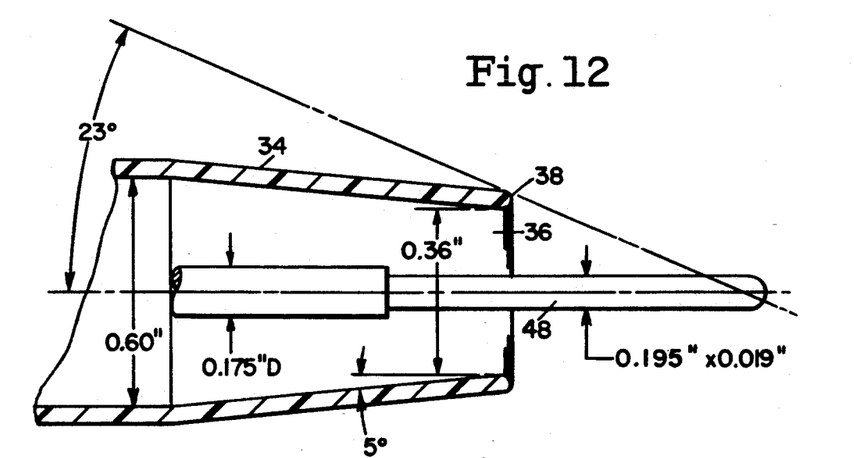
FIG. 12 is a cross-sectional view respectively of the suction intake cone, demonstrating the radiused leading edge.

FIGS. 1-13 illustrate a particular embodiment of a disposable hand-actuated electrosurgical pencil with integral smoke evacuation. FIG. 1 illustrates an electrosurgical instrument assembly 20 comprising an electrosurgical handpiece 22, a length of insulated cable 24 with one end leading out of the distal end of the electrosurgical instrument 22 and other end of the cable 24 leading into an electrical connector 26, see FIG. 15. The connector 26 attaches to a standard operating room RF generator power supply (not shown). The electrosurgical instrument 22 also terminates at the distal end in a standard ribbed vacuum tube connector 28 to which is attached by press-fitting a standard 5 mm internal diameter non-conductive connecting tube 30 with funnel-funnel or other standard ends. The other end of the connecting tube 30 is attached to a standard operating room suction canister (not shown). The suction canister (not shown) is attached to a standard operating room wall vacuum line (not shown). At the proximal end, closest to the patient, the instrument 22 ends in a truncated suction intake cone 34 with an annular suction intake aperture 36. The leading edge 38 of the truncated cone 34 is radiused or beveled and smooth. This leading edge 38 forms the annular aperture 36. The annular aperture 36 encircles, for instance, a standard 2.4 mm interchangeable electrode blade 48, which protrudes beyond the annular aperture. FIG. 12 illustrates the truncated cone 34, which is of a design that gives it a base diameter, length, taper, and aperture diameter that allows all of the generated smoke to be evacuated while giving the surgeon good visibility of the electrode blade tip 48 at all angles of use. This design is discussed in detail subsequently.

Figure 3:
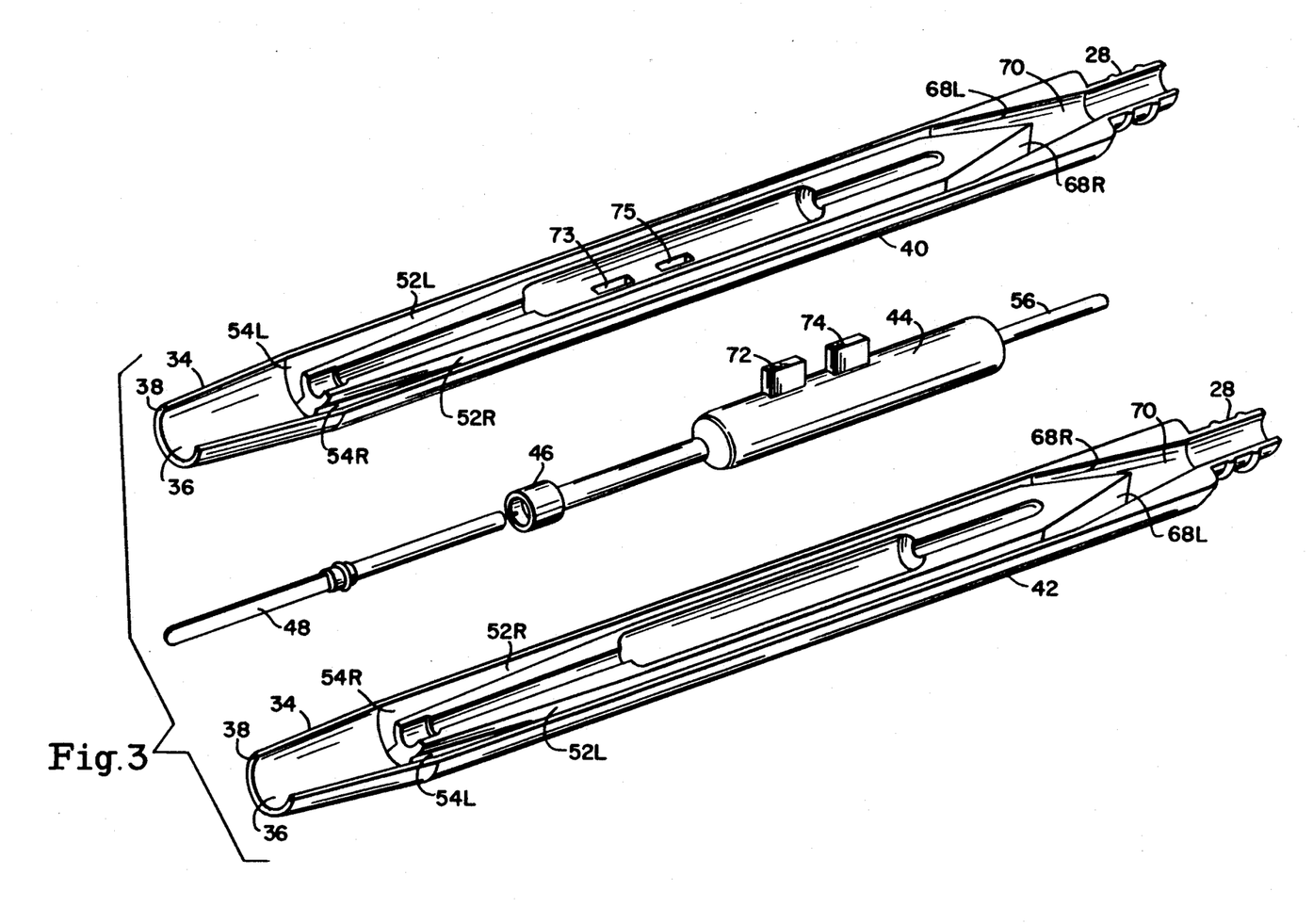
FIG. 3 is an exploded perspective view of the electrosurgical pencil.
Figure 4:
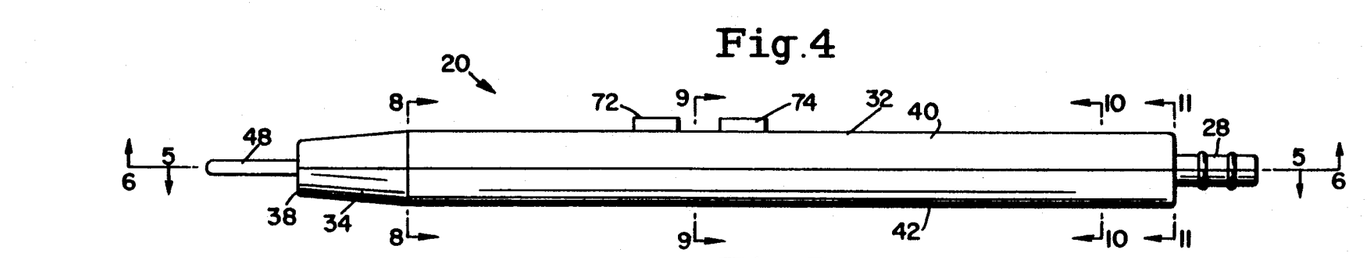
FIG. 4 is a side view of the electrosurgical pencil.

The elongated external housing 32 may be manufactured in two halves or sections, a top section 40 and a bottom section 42, and is of such a design that the sections may be lined up and easily mated during the manufacturing process. An inner sealed electrical switching core 44 nests within the housing 32, in an enlarged hollow region as shown in FIG. 3. The core 44 consists of a standard 2.4 mm chuck 46 which accepts standard interchangeable electrode blades 48 with 2.4 mm bits. The chuck 46 is attached to the sealed switching core 44 which terminates at the other end in an electrical contact 56 to which the insulated electrical cable 24 is attached. The cable 24 runs from the electrical contact 56 to the point 58 where it exits from the rear of the top section of the elongated external housing 40. From this point of exit 58, the cable 24 is bonded with the vacuum connecting tube 30. The switching core 44 has two push buttons 72 and 74 described subsequently, the switches extending through appropriately positioned openings in the housing 20. The switching core 44 is disclosed in U.S. Pat. No. 4,545,375, that part of the patent that deals with the core 44 being incorporated herein by reference.

Figure 5:
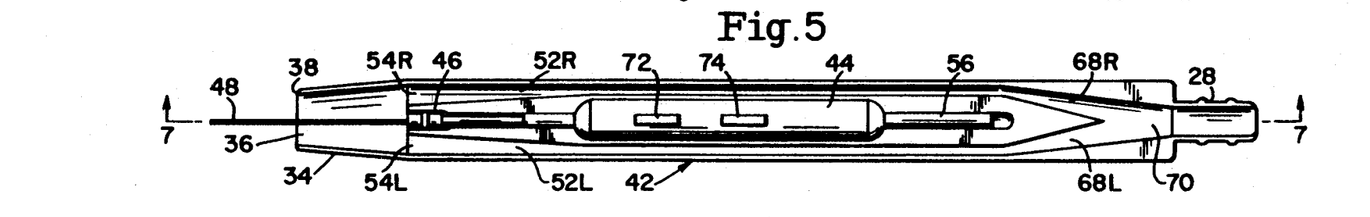
FIG. 5 is a cross-sectional view of FIG. 4 taken along lines 5—5, showing the bottom section of the external housing.
Figure 10:
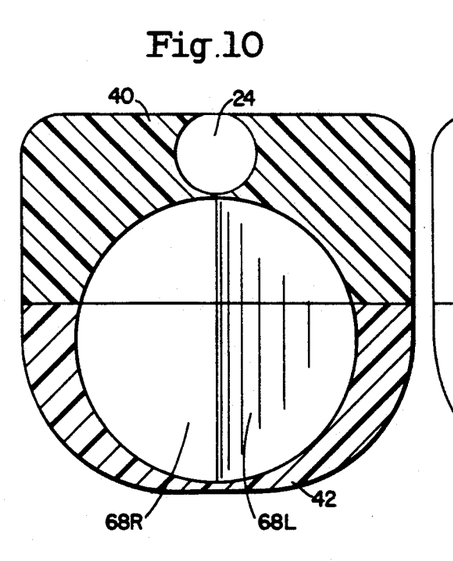
FIG. 10 is a cross-sectional view of the rear portion of FIG. 4, taken along lines 10—10.
Figure 11:
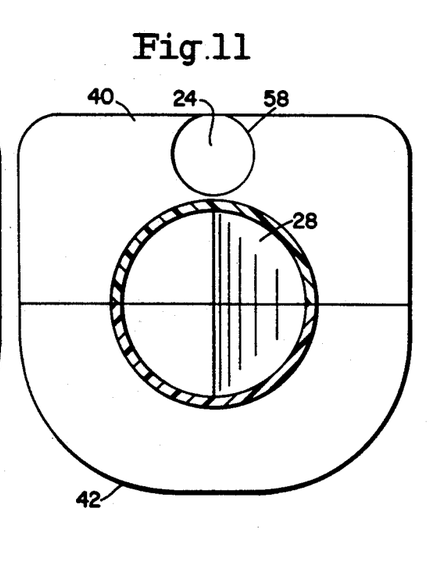
FIG. 11 is an end view of the distal end of FIG. 4, taken along lines 11—11.

FIGS. 3 and 5 illustrate the bottom section 42 of the elongated external housing 32, containing the right 52R and left 52L internal arcuate suction channels, which begin at the proximal end of the elongated external housing 32 closest to the patient, where the base of the truncated suction intake cone 34 joins the elongated external housing 32. The internal suction channels 52R and 52L each have their respective lower section of their intake openings 54R and 54L in the proximal end of the bottom section 42 of the external housing 32, as shown in FIG. 3. As illustrated in FIGS. 5, 7, 8 and 9, the internal suction channels 52R and 52L diverge from their origin at the suction channel intake openings 54R and 54L as they run distally to allow room within the housing 32 for the sealed electrical switching core 44 to rest against the inner wall of the bottom section 42 of the external housing 32. The entire inner electrical core 44 at all points along its length is supported in such a way by the inner wall of the bottom section 42 of the external housing 32 that adequate mechanical support is given to the electrical core 44. Distal to the electrical switching core 44, the internal suction channels 52R and 52L reconverge and then terminate in the right and left internal exhaust ports 68R and 68L, as illustrated in FIGS. 5 and 10. The internal exhaust ports 68R and 68L open into the proximal end of an exhaust plenum 70. The exhaust plenum 70 opens at its distal end into the lumen of the standard external vacuum tube connector 28.

The inner electrical core 44 is sealed and isolated at all points along its length from the internal suction channels 52R and 52L and from the exhaust plenum 70. Each suction channel 52R and 52L and their respective intake openings 54R and 54L and internal exhaust ports 68R and 68L are of such a design that they have an adequate cross-sectional area to allow a flow and velocity of air sufficient to evacuate all of the smoke generated by the electrosurgical pencil as described in detail below.

Figure 6:
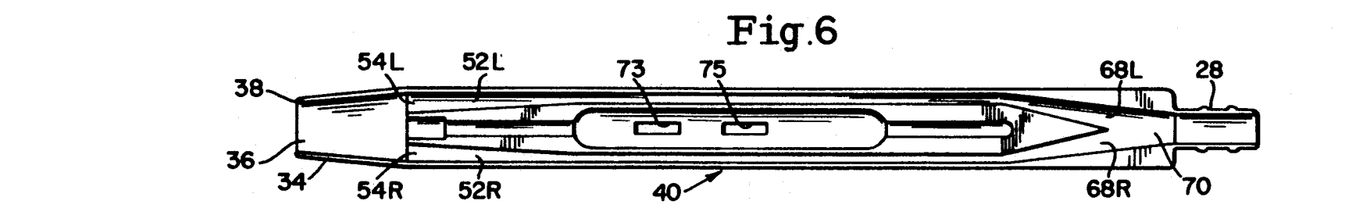
FIG. 6 is a cross-sectional view of FIG. 4 taken along lines 6—6, showing the top section to the external housing.
Figure 7:
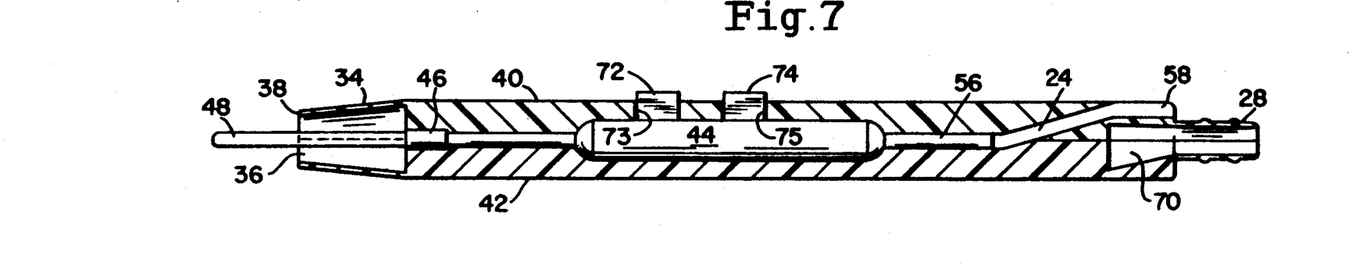
FIG. 7 is a cross-sectional view of FIG. 5 taken along lines 7—7, showing the right section of the external housing.
Figure 8:
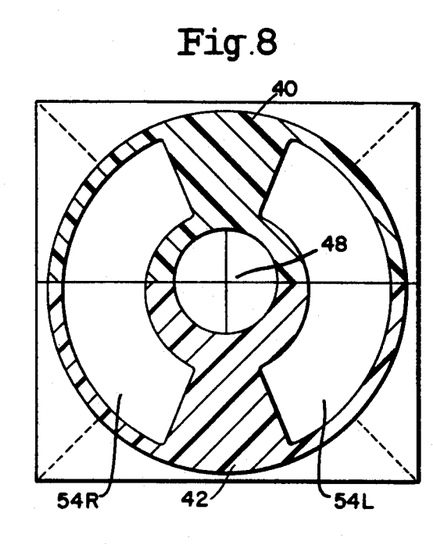
FIG. 8 is an end view of the proximal end of FIG. 4, taken along lines 8—8.
Figure 9:
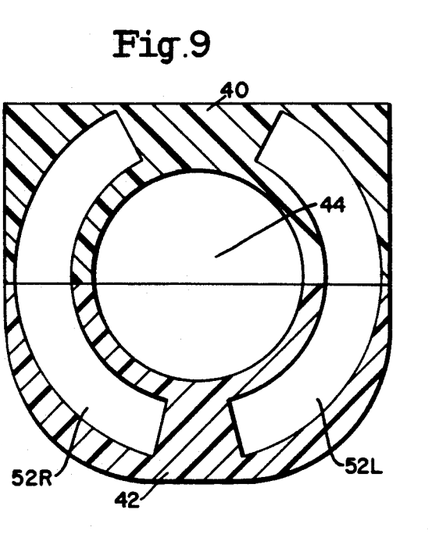
FIG. 9 is a cross-sectional view of the mid-portion of FIG. 4, taken along lines 9—9.

FIGS. 3 and 6 illustrate the top section 40 of the external housing 32. The housing 40 is molded to allow the inner electrical core 44 to nest against the inner wall of the housing 40, providing support for the electrical core 44 and isolating it from the internal suction channels 52R and 52L. The top section of the housing also provides cutouts for the external spring biased electrical switches 72 and 74 employed to change the waveform of the voltage for cutting and cauterizing. At the distal end of the housing 40, the top section of the exhaust plenum 70 penetrates into the top section of the external housing 40, but does not violate the isolation of the electrical cable 24 as it runs from the electrical contact 56 to its exit point 58 from the rear of the top of the external housing 40. The switches 72 and 74 extend upwardly from the switch 44 through openings 73 and 75, respectively, in the top section 40 of the housing.

Figure 15:
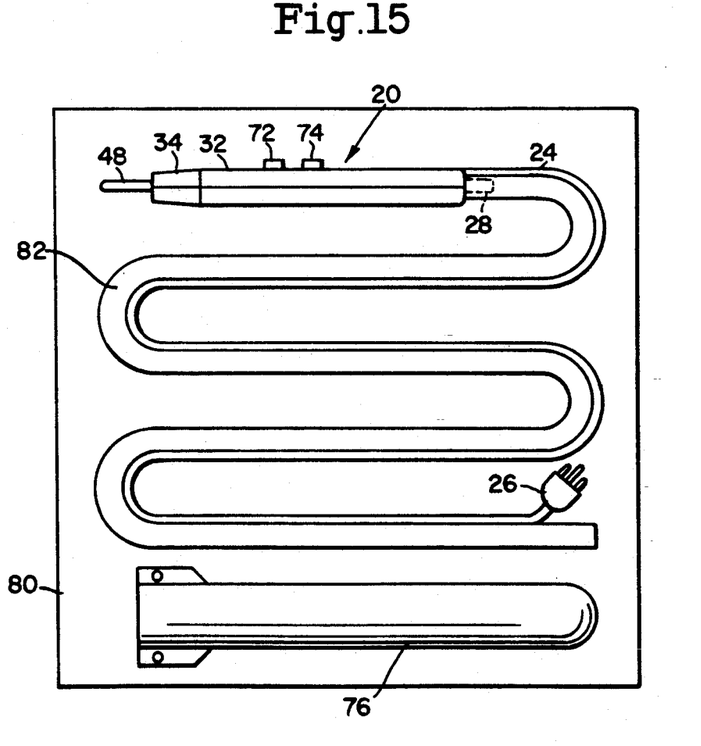
FIG. 15 is an illustration of the instrument packaged and ready to use.

As illustrated in FIGS. 1, 2 and 15, after the electrical cable 24 exits from the rear of the top section of the external housing 40 at point 58, it joins with the suction connecting tube 30. The cable 24 is non-permanently bonded to the external wall of the suction connecting tube 30 for their entire length, starting at distal end of the electrosurgical pencil 22 and continuing until the cable 24 terminates in an electrical connector 26 and the suction tubing 30 terminates in a standard end. This bond may be easily peeled apart.

FIG. 15 illustrates the sterile, disposable electrosurgical instrument assembly 20 as it is packaged and ready to use by the end user. The electrosurgical instrument 22 has a one inch interchangeable electrode blade 48 with a 2.4 mm bit mounted in the 2.4 mm chuck 46 at the proximal end of the inner electrical core 44. At the distal end of the electrosurgical instrument 22, the standard end of an adequate length of 5 mm internal diameter suction connecting tube 30 is press-fitted onto the external standard suction tube connector 28. As the insulated electrical cable 24 exists from the rear of the top section of the external housing 40 at point 58, it is joined to the suction connecting tube 30 by a non-permanent bond. The electrical cable 24 is adequate in length, and ends in a standard electrical connector 26. The joined electrical cable and suction tubing 82 is folded along side the electrosurgical instrument 22 and the whole instrument assembly 20 is contained within an easy-to-open sterile packaging 80, ready to use. Included in the sterile packaging 80, is a disposable holster 76 to secure the instrument 22, on the field when it is not in use.

Figure 13:
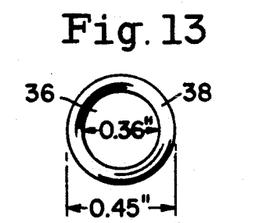
FIG. 13 is an end view of the suction intake cone proximal end.
Figure 14:
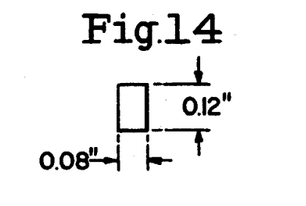
FIG. 14 is a front view of a switch bypass channel.

An exemplary design of a shroud and vacuum passages of a pencil are based upon the dimensioned drawings of FIGS. 12, 13 and 14. The following parameters are assumed in the design of a shroud: The blade tip does not penetrate the tissue; a typical angle of inclination of the pencil is 35°–45°. A minimum clearance of 5° from the tissue is assumed; the maximum off-axis visual obstruction of incision site is no greater than 25°.

Critical ratios are blade cross-sectional area to inlet cross-sectional area and inlet diameter to length of protruding blade. Thus in the present design blade cross-sectional area/inlet cross-sectional area $0.00205/0.1 = 2 \times 10^{-2}$ and inlet diameter/length of protruding blade is $0.45/0.75 = 0.6$. More generally the blade cross-sectional area must be quite small relative to the inlet cross-sectional area of the shroud and the blade length must be large relative to the inlet diameter of the shroud.

It should immediately be noted that FIG. 14 illustrates a configuration of the vacuum passages at the switch bypass region of an earlier design. The present design of FIGS. 3 and 8, for instance, provide improved results relative to that calculated below, since the switch bypass passages are about 50% larger than in the old design.

The design must be such that the pressure drop through the pencil must be less than that of the vacuum source, the drop in the switch bypass passages and the tubing to the vacuum source being the most significant.

Initially the areas of the various elements of the system must be calculated. The area of the blade 48, $A_0 = (0.105 \times 0.020)$ is 0.0021 in². The area $A_1$, the inlet area of the shroud, is the area of the opening less the area of the blade or $A_1 = 0.100$ in². The nozzle outlet area $A_2$ is the area of the shroud again less the blade area or $A_2 = 0.258$ in². The switch bypass area, $A_3$, of the two channels of the original design was $A_3 = 0.02$ in² and the area $A_4$ of the 5 mm section tubing is $A_4 = 0.0304$ in².

The volume flow rate V, available from the vacuum source is $V = 50.853$ ins³/sec based on a 50 liter/minute flow rate available from the vacuum source. The speed of sound, $a_0$ at 70° F. (530° R.) is $a_0 = 1128.4$ ft/sec.

The velocities at various locations using the aforesaid areas and flow rates are inlet velocity $V_1$ $V_1 = 42.378$ ft/sec, outlet velocity, $V_2$ $V_2 = 16.425$ ft/sec, switch bypass velocity, $V_3$ $V_3 = 220.7$ ft/sec, and 5 mm tube entrance velocity, $V_4$ $V_4 = 139.24$ ft/sec.

The Reynolds numbers at the entrance to the tubing is approximately 14,550 and at the outlet is approximately 24,365.

With the above information it is determined that the pressure drop in the tubing is approximately 14.5 in. Hg and in the switch bypass 0.75 in. Hg for a total pressure drop of any significant amount of approximately 15.25 in. Hg. The inches of mercury head in a standard operating room system is 20–28 in. Hg so that the design is valid even before enlarging the vacuum channels. Further with a shroud inlet velocity of 42.378 ft/sec the ratio to the smoke dispersion rate of 10 to 15 ft/sec is worst case 2.82 to 1 and best case is 4.2 to 1. With the new design of the switch bypass channels the worst case ratio easily exceeds the 2:1 ratio.

OPERATION

The manner of using the electrosurgical pencil with integral smoke evacuation is identical to using the single purpose electrosurgical pencil. After the sterile packaging 80 is opened and the sterile instrument assembly 20 is placed by the scrub nurse on the operating field, the surgeon secures the provided holster 76 and a length of joined electrical cable and tubing 82 to the surgical drape in his or her customary fashion. The electrical connector 26 and joined cable and tubing 82 are then passed off the surgical field to the circulating nurse, who connects the standard end of the suction tubing 30 to a standard suction canister (not shown) and turns the vacuum on. An adequate length of electrical cable 24 is separated from the joined tubing and cable 82, and the electrical connector 26 which terminates the cable 24 is plugged into a radio frequency power generator, also commonly called a Bovie unit (not shown). The unit is turned on and power is set according to the surgeon's wishes. The circulating nurse also attaches to the patient a self-adhesive passive electrical grounding pad (not shown) so that the electrical circuit is complete. When the electrode blade tip is placed in proximity to the area to be cut or cauterized, and the surgeon actuates the appropriate switch 72 or 74, a current which produces heat locally is applied to the tissue. As the tissue heats up, smoke comprised of steam, carbon and other particulates, vaporized and aerosolized organic material, and possibly viable viral particles, is produced. With integral smoke evacuation, when smoke is generated at the electrode blade tip 48, the smoke is drawn continuously and unobtrusively into the annular suction intake aperture 36 at high velocity, allowing no smoke to escape and disperse above the field. No extra hands or personnel are needed, and the surgeon operates as if he is using an electrosurgical pencil alone. The smoke is completely evacuated from the surgical field with the instrument 22 held parallel or perpendicular to the field, or at any angle in between. Smoke evacuation is complete no matter how the instrument 22 itself is rotated. The radiused leading edge 38 of the intake aperture 36, which is rounded and smooth, effectively decreases airflow turbulence at the edge. This allows a greater airflow velocity and more efficient smoke evacuation. The smooth leading edge 38 also presents a nontraumatic surface to tissue with which it may come in contact.

The annular intake cone 34 is fixed, and there are no other parts to manipulate or to slide in order to effect smoke evacuation. The tip of the electrode blade 48 is never obscured and extends sufficiently from the shroud that it may be readily cleaned by scraping and/or wiping. Residue that adheres to the blade tip 48 may be easily cleaned off without interference from the leading edge 38 of the entry aperture of the cone 34. After the smoke is drawn in through the annular intake aperture 36, it continues through the intake openings 54R and 54L, and is conducted along the internal suction channels 52R and 52L, and then through the internal exhaust ports 68R and 68L into the internal exhaust plenum, where it is then evacuated through the lumen of the external standard suction tube connector 28, and into the suction tubing 30, where it enters the operating room's vacuum system. Any electrically conductive liquid or other material that is evacuated into the instrument's suction channels is isolated from the sealed inner electrical core 44, so that there is no electrical burn hazard to the operator or risk of short-circuiting the instrument. The instrument 22 has no extra parts to move, slide of manipulate, and it maintains the same feel and balance as an electrosurgical pencil alone. After completion of the surgery, the entire instrument assembly 20 may be disposed of in the same manner as an electrical pencil alone, so that each patient has a new, sterile instrument.

The intake cone with its annular opening is of such a design that its length, taper, base diameter, and apex diameter, as well as its radiused leading edge, have been calculated to give the surgeon full view of the electrode blade tip while also minimizing airflow turbulence at the opening so that maximum airflow is achieved and all of the smoke is trapped. It is noted from the above calculations that the Reynolds number is 14,500 which is in the range just above where the flow is unstable as between laminar and turbulent flow. At Reynolds numbers of 2,000 and below flow is laminar. In the range of 2,000 to 12,000 the flow is unstable becoming laminar or turbulent depending upon initial turbulence. Above 12,000 the flow is turbulent but at 12,500 it is not violently turbulent so that in the present device the airflow turbulence is not a material problem and head loss is not great.

As indicated above, the pressure or head loss at the switch bypass region is large due to narrowing of the passages. It has been found however that with the arcuate configuration of vacuum channels illustrated in the various figures as opposed to the small rectangular channels upon which the above calculations were based the loss of pressure is reduced and performance is increased.

While the above description contains many specificities, these should not be construed as limitations on the scope of the invention, but rather as an exemplification of one preferred embodiment thereof. Those skilled in the art can appreciate that many other variations are possible without departing from the spirit and scope of this invention. For example, the internal suction channels, their intake openings and exhaust ports, the exhaust plenum may be of different cross-sectional geometric shapes that provide adequate cross-sectional area to allow sufficient airflow and velocity to evacuate all of the generated smoke. The suction channels may be either internal or external to the external housing of the instrument, and may number one or more in any configuration.

The electrode blade may be interchangeable or fixed, and may be of any length or shape so long as the requisite ratios are maintained, and may have a bit conforming to the 2.4 mm standard or to any other standard or diameter. The suction intake cone may be permanently fixed or detachable; it may be of any base diameter and aperture diameter and of any taper or length so long again as the requisite ratios are not materially altered whereby to allow adequate airflow to evacuate all of the smoke generated and that at the same time allows adequate visibility of the electrode blade tip by the surgeon. The electrical cable may exit from the external housing of the instrument at any point along its length. The electric cable and suction tubing may be joined or not joined, and may be joined by any method, permanent or not. The inner electrical core may rest on support ribs or struts, or on the inner wall of the housing, or rest in the housing using any method that gives it adequate mechanical support. The electrical switches may be in any shape, and be located on the external housing in their customary or other convenient location. The instrument may be hand-controlled or foot-controlled. The external housing and suction intake cone may be made of any material, and be of any color, and may be transparent or opaque. The elongate external housing may be in any shape that allows it to be comfortably gripped by a human hand.

Although the present invention has been described for an electrosurgical instrument; embodiments of this invention include integral smoke, fume, and suspended particulate evacuation at the point of generation by all tools and instruments held by a human hand or robotic or mechanical arm that cause generation of smoke, fumes, or suspended particulates at their point of use during their normal operation. Such uses can be soldering, welding, cutting of materials particularly plastic by a heated electrode or the like. These embodiments maintain all of the objects, advantages, and ramifications cited for the electrosurgical instrument.

While one embodiment of the invention has been described in detail, it will be apparent to those skilled in the art that the disclosed embodiment may be modified. Therefore, the foregoing description is to be considered exemplary rather than limiting, and the true scope of the invention is that defined in the following claims.

I claim:

1. An electrosurgical pencil comprising
   a tubular body having a proximal end and a distal end and at least one passage extending generally the length of said body from the distal end to the proximal end,
   means for connecting said passage to a source of vacuum,
   an electrode blade extending from the proximal end of said body,
   an electrical conductive means extending at least partially through said body to contact said electrode blade adjacent said proximal end and to extend out of said body to be connectable to a source of electrical energy,
   a hollow shroud extending from the proximal end of said body and positioned about a predetermined length of said electrode blade,
   said passage having an inlet opening in said proximal end within said shroud,
   said passage and said means for connecting configured such that the velocity of the airflow into said shroud is in a range approximately twice and greater than the expansion velocity of smoke produced by said electrode blade.

2. An electrosurgical pencil according to claim 1 further comprising
   a second passage extending the length of said body, and
   means for connecting said second passage to a source of vacuum.

3. An electrosurgical pencil according to claim 2 wherein said passages are arcuate.

4. An electrosurgical pencil according to claim 3 wherein said passages are diametrically opposed in said body.

5. An electrosurgical pencil according to claim 4 wherein
   said shroud has an entrance opening,
   the area of said entrance opening being substantially greater than the cross-sectional area of said electrode blade.

6. An electrosurgical pencil according to claim 2 wherein said passages merge adjacent the distal end of said body.

7. An electrosurgical pencil according to claim 2 wherein
   said means for connecting includes tubing; and
   said passages and said tubing produce flows adjacent the entrance opening of said shroud with Reynolds numbers in the low turbulent range.

8. An electrosurgical pencil according to claim 1 wherein
   said shroud tapers inwardly away from said body.

9. An electrosurgical pencil according to claim 1 wherein
   said body has a longitudinal axis; and
   said shroud has a size and length relative to the length of said electrode blade such that the off-axis visual obstruction of an incision site is no greater than approximately 25°.

10. An electrosurgical pencil according to claim 1 wherein
    said shroud is configured relative to said body and said electrode blade such as to provide at least a 30° surface clearance angle.

11. An electrosurgical pencil according to claim 1 wherein
    said shroud provides an annular space about said electrode blade.

12. An electrosurgical pencil according to claim 1 wherein said shroud is transparent.

13. An electrosurgical pencil according to claim 1 further comprising
    means for removing and replacing said electrode blade.

14. An electrosurgical pencil according to claim 1 comprising
    means for removably securing said shroud to said tubular body.

15. An electrosurgical pencil according to claim 1 wherein the velocity of the airflow into said shroud is in the range of approximately 20 to 60 feet per second.

16. An electrosurgical pencil comprising
    a tubular body having a proximal end and a distal end and at least one passage extending the length of said body,
    means for connecting said passage to a source of vacuum,
    an electrode blade extending from the proximal end of said body and having an end remote from the body,
    an electrical conductor extending at least partially through said body to contact said electrode blade adjacent said proximal end,
    means adjacent the distal end of said body for conductively connecting said conductor to a source of electrical energy, a hollow shroud extending from the proximal end of said body and positioned about a predetermined length of said electrode blade, said passage having an inlet opening adjacent said proximal end within said shroud, said shroud being generally conical with its base adjacent the proximal end and having an apex directed away from the proximal end of the body and an apex diameter and length relative to the diameter and length of said electrode blade to permit sufficient air flow at the apex of the shroud to trap smoke generated by the electrode blade and far enough from the end of the blade to provide an unobstructed view of the end of the electrode blade by the user.

17. An electrosurgical pencil according to claim 16 wherein said pencil having a longitudinal axis;

said shroud has a size and length relative to the length of said electrode blade such that the off-axis visual obstruction of an incision site is no greater than approximately 25°.

18. An electrosurgical pencil according to claim 16 wherein said shroud is configured relative to said body and said electrode blade such as to provide at least a 30° surface clearance angle.

19. An instrument employing a heater member which when employed for its intended purpose generates a quantity of smoke that it is desirable to remove from adjacent the heater member comprising the heater member having a work performing end, a body supporting said heater member, a hollow generally conical shroud disposed about said heater member, and having an apex directed away from said body;

said apex disposed adjacent the work performing end of said heater member, means for producing a vacuum interiorly of said shroud, said apex end of said shroud being located far enough from said work performing end of said heater member to provide to an individual utilizing said instrument an unobstructed view of the work performing end of the heater member, said shroud having an apex diameter relative to the diameter of said heater member and having its apex located sufficiently close to said work performing end of said heater member to permit a sufficient flow of gases into said apex end of said shroud to trap smoke generated by the heater member.

* * * * *